United States Patent
Finn et al.

(10) Patent No.: US 10,993,746 B2
(45) Date of Patent: May 4, 2021

(54) HEAD TO HEAD TRANSVERSE CONNECTOR

(71) Applicant: K2M, Inc., Leesburg, VA (US)

(72) Inventors: Michael Finn, Aurora, CO (US); Christopher Harrod, Baton Rouge, LA (US); Sergey Neckrysh, Chicago, IL (US); Peter Newton, La Jolla, CA (US); Harry Shufflebarger, Jupiter, FL (US); Timmon Ark, Vienna, VA (US); Theo Choi, Arlington, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 16/401,173

(22) Filed: May 2, 2019

(65) Prior Publication Data
US 2019/0336178 A1   Nov. 7, 2019

Related U.S. Application Data

(60) Provisional application No. 62/666,313, filed on May 3, 2018.

(51) Int. Cl.
*A61B 17/70*   (2006.01)

(52) U.S. Cl.
CPC ...... *A61B 17/7049* (2013.01); *A61B 17/7032* (2013.01); *A61B 17/7037* (2013.01)

(58) Field of Classification Search
CPC .............. A61B 17/7049; A61B 17/705; A61B 17/7052
See application file for complete search history.

(56) References Cited

U.S. PATENT DOCUMENTS

| | | | |
|---|---|---|---|
| 5,938,663 A | * | 8/1999 | Petreto ............... A61B 17/7041 606/278 |
| 8,672,978 B2 | * | 3/2014 | Dant .................... A61B 17/705 606/250 |

(Continued)

FOREIGN PATENT DOCUMENTS

| | | | |
|---|---|---|---|
| EP | 1762195 A1 | 3/2007 | |
| FR | 2719759 A1 | * 11/1995 | ......... A61B 17/7052 |
| FR | 2720923 A1 | * 12/1995 | ......... A61B 17/7032 |

OTHER PUBLICATIONS

English Machine translation for FR 2719759, accessed Jul. 6, 2020.*

(Continued)

*Primary Examiner* — Jan Christopher L Merene
(74) *Attorney, Agent, or Firm* — Lerner, David, Littenberg, Krumholz & Mentlik, LLP

(57) ABSTRACT

A transverse connector includes a cross member assembly, a first connector assembly, and a second connector assembly. The cross member assembly includes a cross member, a first ring, and a second ring. The cross member has a first end portion and a second end portion. The first ring is receivable on the first end portion of the cross member and the second ring is receivable on the second end portion of the cross member. The first and second connector assemblies are coupled to the first and second rings of the cross member assembly, respectively, to support the cross member between the first and second connector assemblies. The first and second connector assemblies are configured to selectively and releasably secure to bone anchors.

18 Claims, 5 Drawing Sheets

(56) References Cited

U.S. PATENT DOCUMENTS

| | | | |
|---|---|---|---|
| 8,920,475 B1 | 12/2014 | Ziemek et al. | |
| 9,247,964 B1 | 2/2016 | Shoshtaev | |
| 2004/0147929 A1* | 7/2004 | Biedermann | A61B 17/7001 606/266 |
| 2005/0010216 A1* | 1/2005 | Gradel | A61B 17/7041 606/264 |
| 2005/0228326 A1* | 10/2005 | Kalfas | A61B 17/7007 602/19 |
| 2006/0064091 A1* | 3/2006 | Ludwig | A61B 17/1671 606/250 |
| 2008/0172093 A1 | 7/2008 | Nilsson | |
| 2009/0187217 A1 | 7/2009 | Weiman et al. | |
| 2009/0264931 A1* | 10/2009 | Miller | A61B 17/704 606/251 |
| 2011/0071569 A1 | 3/2011 | Black | |
| 2012/0271355 A1* | 10/2012 | Steele | A61B 17/7089 606/264 |
| 2013/0172934 A1 | 7/2013 | Walker et al. | |
| 2018/0014861 A1* | 1/2018 | Shoshtaev | A61B 17/7032 |

OTHER PUBLICATIONS

Machine English Translation of FR 2720923, http://ww.epo.org, accessed Oct. 8, 2020.*
European Search Report from EP 19172236.2, dated Sep. 24, 2019, pp. 1-10.

\* cited by examiner

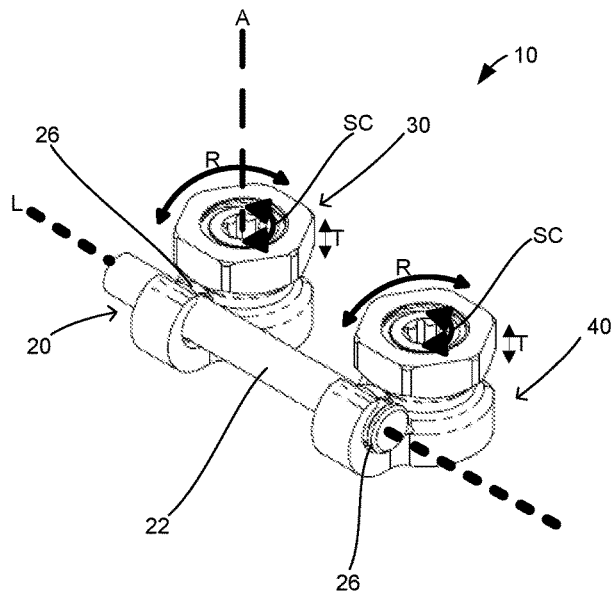
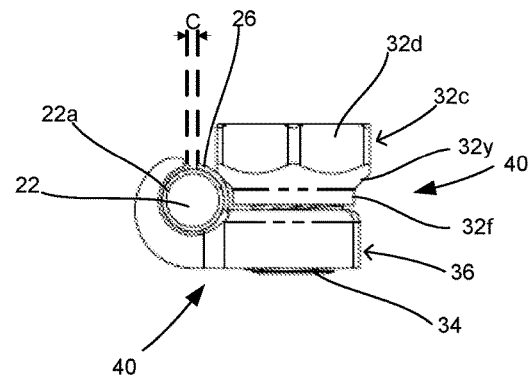
FIG. 3
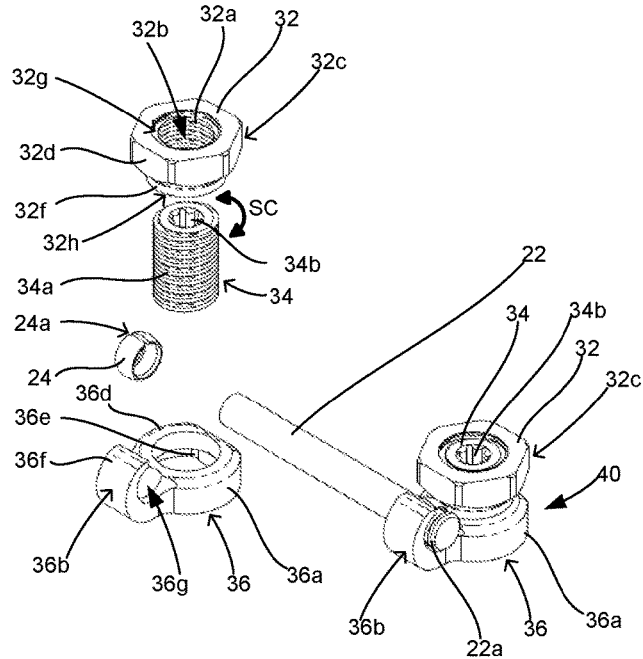
FIG. 2
FIG. 1

HEAD TO HEAD TRANSVERSE CONNECTOR

CROSS-REFERENCE TO RELATED APPLICATIONS

The present application claims the benefit of the filing date of U.S. Provisional Patent Application No. 62/666,313 filed May 3, 2018, the disclosure of which is hereby incorporated herein by reference.

TECHNICAL FIELD

The present disclosure relates to a device for interconnecting bone anchors and, more particularly, to a transverse connector that couples heads of bone anchors together.

BACKGROUND

Disease, the effects of aging, or physical trauma resulting in damage to the spine has been treated in many instances by fixation or stabilization of the effected vertebra. A wide variety of spinal fixation apparatuses have been employed in surgical procedures for correcting spinal injuries and the effects of spinal diseases. Many of these apparatuses commonly use a pair of longitudinal rods running in a relatively parallel relationship to each other and the spinal column. These rods are connected to connectors, which in turn are secured to the underlying vertebral bone by spinal bone fixation fasteners such as pedicle screws, hooks, and the like. The pair of longitudinal rods can be held in position relative to one another by transverse connectors, also known as transverse bridge elements or cross-connectors.

SUMMARY

The present disclosure is directed to a transverse connector that includes a cross member assembly, a first connector assembly, and a second connector assembly. The cross member assembly includes a cross member, a first ring, and a second ring. The cross member has a first end portion and a second end portion. The first ring is receivable on the first end portion of the cross member and the second ring is receivable on the second end portion of the cross member. The first and second connector assemblies are coupled to the first and second rings of the cross member assembly, respectively, to support the cross member between the first and second connector assemblies. The first and second connector assemblies are configured to selectively and releasably secure to bone anchors.

In some embodiments, the first connector assembly may include a mount configured to seat the first connector assembly on a first bone anchor of the bone anchors. The first connector assembly may include a screw receivable through the mount. The screw may be engagable with the first bone anchor. The first connector assembly may further include a nut that threadably engages the screw to selectively secure the first connector assembly to the first bone anchor. The nut may be configured to tighten against the first ring to tighten the first ring around the cross member and fictionally lock the cross member in position relative to the first connector assembly.

In some embodiments, the mount may include a head mount portion and a rod mount portion that extends from the head mount portion. The rod mount portion may be configured to receive the cross member. The rod mount portion may include a hooked arm that curves upward and inward toward the head mount portion. The hooked arm may define a ring groove that is configured to receive the first ring therein. The first ring may be an open ended ring positioned to move between a first position and second position. The first ring may have a first diameter in the first position and a second diameter in the second position. The second diameter may be less than the first diameter. The first ring may be configured to axially lock the cross member to the rod mount portion of the mount when the first ring is in the second position. The cross member may be axially movable relative to the first ring when the first ring is in the first position.

In certain embodiments, the cross member may include an annular flange supported on one of the first and second end portions of the cross member. The annular flange may be configured to limit axial movement of the cross member relative to the first and second connector assemblies.

In another aspect of the present disclosure, a transverse connector includes a cross member, a ring, a first connector assembly, and a second connector assembly. The cross member includes a first end portion and a second end portion. The ring is supported on the first end portion of the cross member. The first connector assembly is coupled to the ring to secure the cross member to the connector assembly. The first connector assembly is configured to selectively and releasably secure to a bone anchor. The second connector assembly is coupled to the second end portion of the cross member.

In some embodiments, the first connector assembly may include a mount and a screw that couple to the bone anchor, and a nut that couples to the screw to secure the cross member to the mount. The nut and the screw may be threadably coupled together. The nut may include a drive portion and a skirt that extends distally from the drive portion. The drive portion may include a distal taper portion that is selectively engagable with the ring as the nut rotates about the screw. The ring may be configured to compress against the cross member as the nut tightens against the ring. The mount may include a hooked arm that supports the ring and the cross member therein.

In accordance with still another aspect of the present disclosure, a spinal system is provided. The spinal system includes a first bone anchor configured to support a first spinal rod, a second bone anchor configured to support a second spinal rod, and a transverse connector that couples the first and second bone anchors together. The transverse connector includes a first connector assembly, a second connector assembly, and a cross member. The first connector assembly includes a first mount coupled to the first bone anchor and supports a first ring. The second connector assembly includes a second mount coupled to the second bone anchor and supports a second ring. The cross member is coupled to the first and second rings and extends between the first and second connector assemblies.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure, wherein:

FIG. 1 is a perspective view of a transverse connector in accordance with the present disclosure;

FIG. 2 is a perspective view, with parts separated, of the transverse connector of FIG. 1;

FIG. 3 is a side view of the transverse connector of FIG. 1;

DETAILED DESCRIPTION

Figure 4:
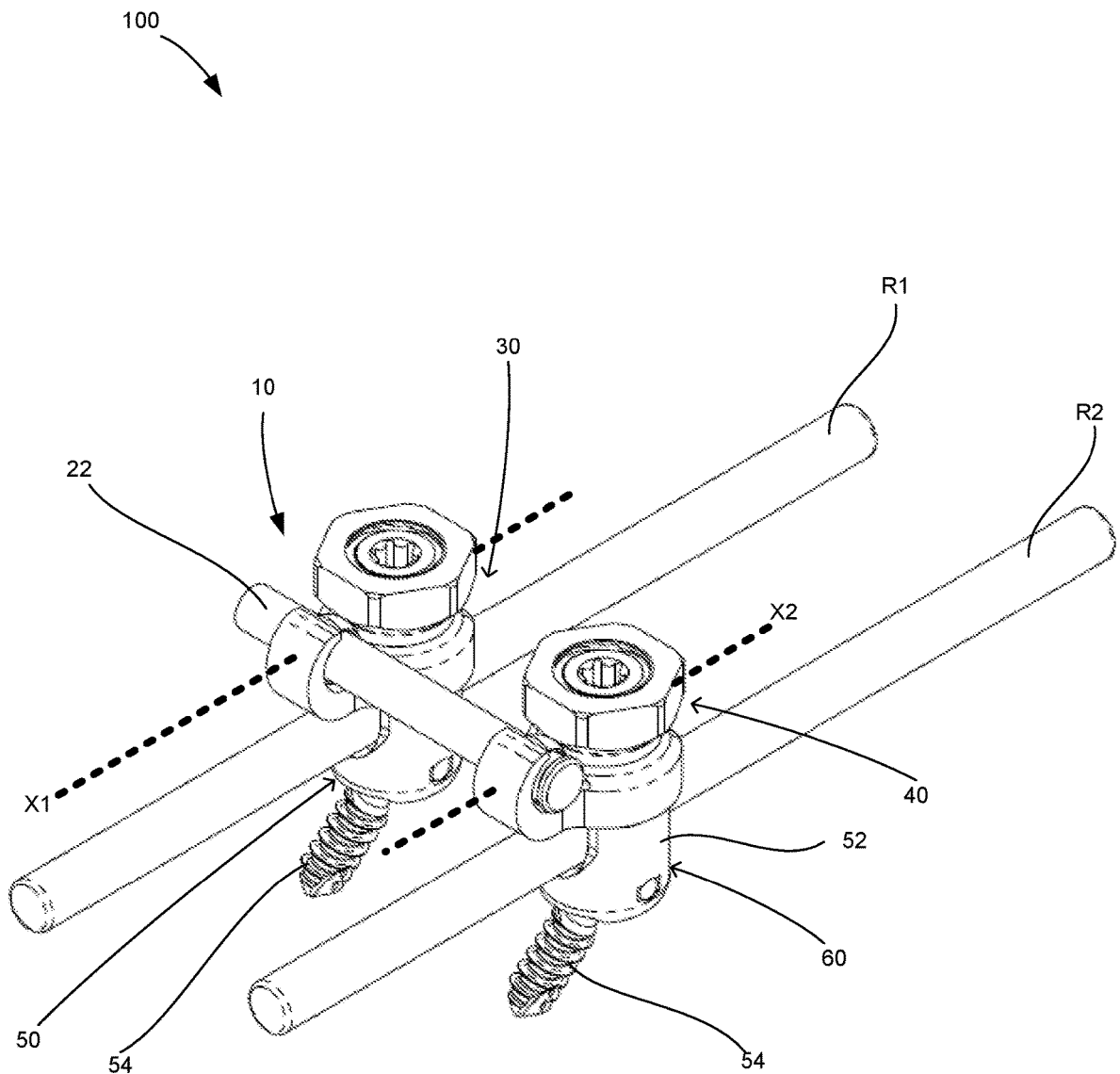
FIG. 4 is a perspective view of one embodiment of a spinal system including a pair of spinal rods, a pair of bone anchors, and the transverse connector of FIG. 1.
Figure 5:
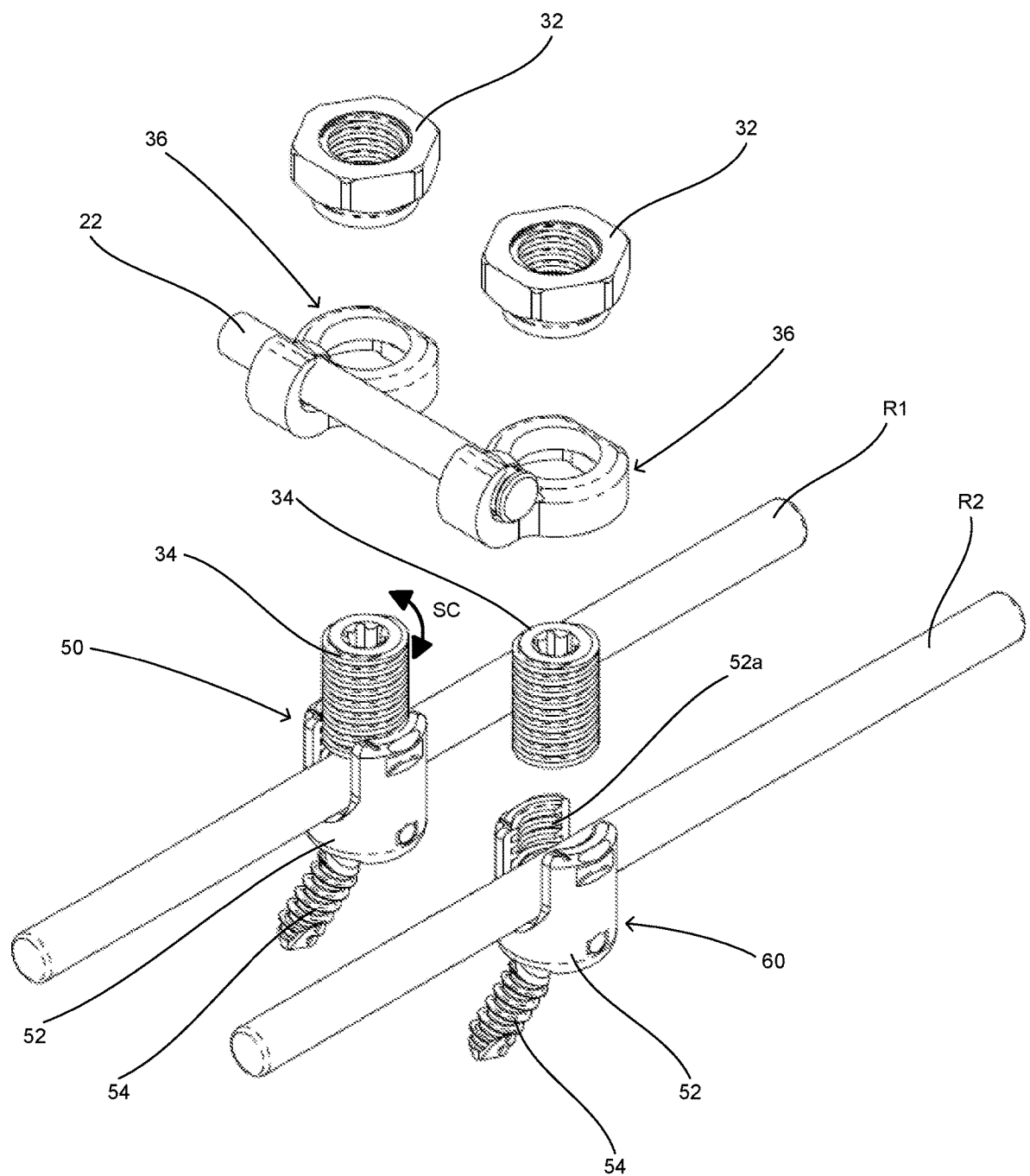
FIG. 5 is a perspective view, with parts separated, of the spinal system of FIG. 4.

Various embodiments will now be described in detail with reference to the drawings, wherein like reference numerals identify similar or identical elements. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

Turning now to FIGS. 1-4, a transverse connector is provided which is generally referred to as transverse connector 10. Transverse connector 10 includes a cross member assembly 20, a first connector assembly 30, and a second connector assembly 40 that is identical to first connector assembly 30. First and second connector assemblies 30, 40 are supported on opposite end portions of cross member assembly 20.

Cross member assembly 20 of transverse connector 10 includes a cross member 22 that defines a long axis "L," a first ring 24 supported on a first end portion of cross member 22, and a second ring 26 supported on a second end portion of cross member 22. Cross member 22 includes an annular flange 22a supported on a first end portion thereof that limits axial movement of cross member 22 along long axis "L" of cross member 22 relative to first and second connector assemblies 30, 40. Cross member 22 further defines bore 22b (FIG. 8) in a second end portion thereof opposite to the first end portion. Bore 22b is configured to receive an instrument (not shown) to control and/or manipulate a position of cross member 22. First and second rings 24, 26 are identical. Each of the first and second rings 24, 26 defines a slot 24a through a thickness of one end thereof (e.g., an open ended ring) and includes a uniform central portion 24b configured to frictionally engage an outer surface of cross member 22. Uniform central portion 24b, is supported between tapered openings 24c, 24d on opposite ends of central portion 24b (see FIG. 8). First and second rings 24, 26 may be at least partially formed of a flexible material. As indicated by arrows "C" (FIG. 3), first and second rings 24, 26 may be configured to move between a first position in which first and second rings 24, 26 have a first diameter, and a second position in which first and second rings 24, 26 have a second diameter that is smaller than the first diameter. Movement of first and second rings 24, 26 between the first and second positions may be effectuated via application or removal of radial compression forces thereto via first or second connector assemblies 30, 40.

Given that first connector assembly 30 is identical to second connector assembly 40, as noted above, only first connector assembly 30 is described in detail herein in the interest of brevity. First connector assembly 30 includes a nut 32, a screw 34 that threadably couples to nut 32, and a mount 36 that receives screw 34 therethrough. Nut 32 includes a threaded inner surface 32a that defines an opening 32b through nut 32, a drive portion 32c on a proximal end portion of nut 32, and a skirt 32f that is recessed from, and extends distally from, drive portion 32c. Skirt 32f is configured to maintain drive portion 32c at a predetermined height above an upper surface of mount 36 to selectively capture ring 24 between drive portion 32c and mount 36 (e.g., pinch a side portion of ring 24 as seen in FIG. 3). Drive portion 32c of nut 32 includes flats 32d supported at spaced apart locations about an outer surface thereof. Drive portion 32c further includes a distal taper portion 32x (e.g., annular taper) that connects drive portion 32c to a proximal portion of skirt 32f of nut 32. Flats 32d are configured to facilitate engagement with a driving instrument (e.g., a socket wrench—not shown) for rotating nut 32 about axis "A," as indicated by arrows "R" (FIG. 1). Internal surface 32a and opening 32b of nut 32 extend along drive portion 32c and skirt 32f of nut 32 to connect apertures 32g, 32h of nut 32 that open on opposite ends of nut 32 (see FIG. 2).

Screw 34 of first connector assembly 30 includes a threaded outer surface 34a that threadably couples to threaded inner surface 32a of nut 32. Screw 34 further includes a drive recess 34b defined in a proximal end portion of screw 34 that is configured to receive a drive tool (e.g., a screw driver—not shown) to rotate screw 34 relative to nut 32 and/or mount 36 about a longitudinal axis "A" defined through screw 34 (e.g., clockwise and/or counter clockwise as indicated by arrows "Sc"). Drive recess 34b can be any suitable configuration such as hexolobular or the like.

Figure 9:
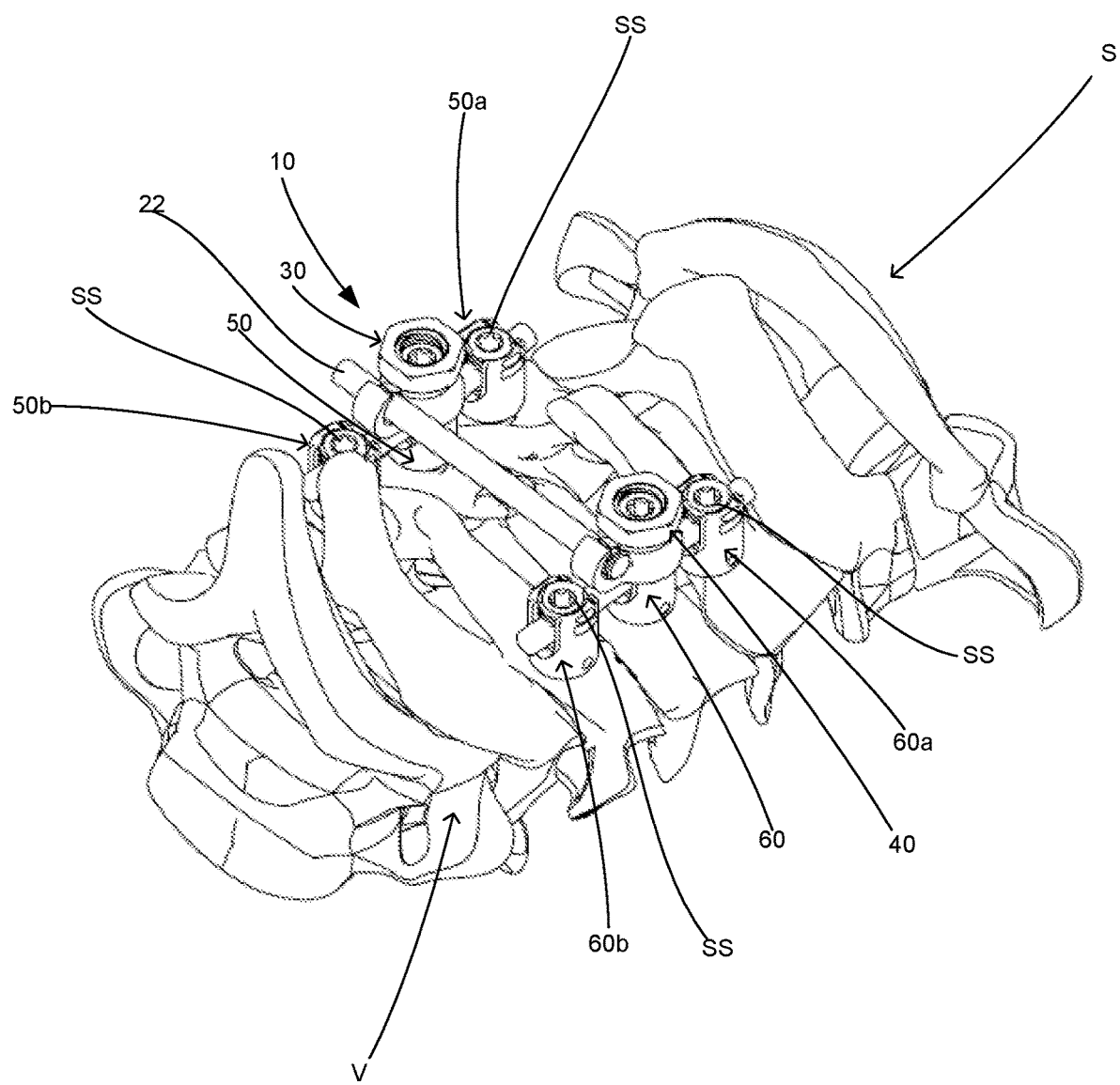
FIG. 9 is a perspective view of another embodiment a spinal system coupled to a spine.

Mount 36 of first connector assembly 30 includes a head mount portion 36a and a rod mount portion 36b. Head mount portion 36a is configured to selectively and releasably secure to a head 52 of a bone anchor 50 (see FIG. 4) that includes a bone screw 54 coupled to head 52 of bone anchor 50 for mounting to a vertebral body "V" of a spine "S" (FIG. 9). Bone anchor 50 may have a set screw arrangement that is configured for polyaxial movement between head 52 and bone screw 54. In some embodiments, bone anchor may have a taper-lock arrangement. For a more detailed description of example set screw and taper lock type bone anchors, reference can be made to U.S. Pat. Nos. 9,393,049 and 8,814,919, the entire contents of each of which are incorporated by reference herein.

Head mount portion 36a of mount 36 defines an opening 36c therethrough that is configured to receive screw 34 therethrough. Head mount portion 36a further includes an upper surface 36d and a lower surface 36e that is keyed to an outer surface of a head 52 of a bone anchor 50. Head mount portion 36a is configured to maintain mount 36 fixed onto a bone anchor 50 so as to prevent mount 36 from rotating clockwise or counter clockwise about longitudinal axis "A" of screw 34 of first connector assembly 30 (e.g., rotatably locked). Rod mount portion 36b is configured to support a first end portion of cross member 22 and includes a hooked arm 36f that curves upward and inward toward head mount portion 36a. Rod mount portion 36b further defines a ring groove 36g along a central portion of an inner surface thereof that is configured to receive first ring 24 therein while cross member 22 is received through first ring 24. Ring groove 36g is recessed within rod mount portion 36b to prevent ring 24 from sliding along rod mount portion 36b (e.g., axially relative to axis "L").

With reference to FIGS. 4 and 6-8, each ring groove 36g of first and second connector assemblies 30, 40 has an arcuate and/or spherical profile that is slightly larger than rings 24, 26 to enable rings 24, 26 to move within respective ring grooves 36g. Each ring groove 36g defines one or more axes therethrough, for instance, axis "X1" through first connector assembly 30, and axis "X2" through second connector assembly 40. Rings 24, 26 are positioned for polyaxial movement within ring grooves 36g so that first and second connector assemblies 30, 40 can be positioned at different angles relative to one another (e.g., vertical displacement such as up or down, as indicated by arrows "U/D," horizontal displacement such as forwards or backwards, as indicated by arrows "F/B," or combinations thereof).

Figure 6:
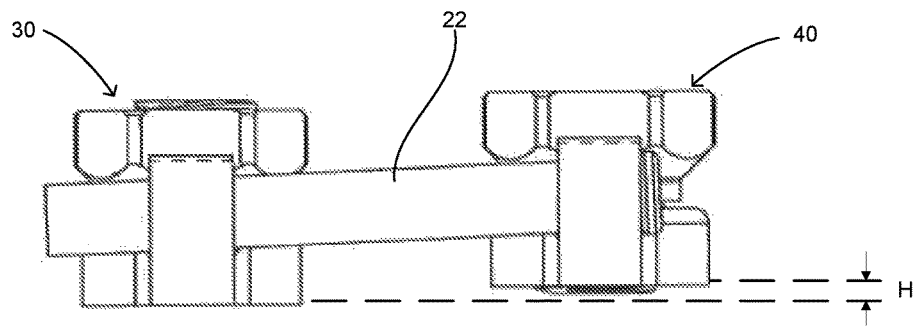
FIG. 6 is a front view of the transverse connector of FIG. 1 with first and second connector assemblies thereof shown positioned offset from one another.
Figure 7:
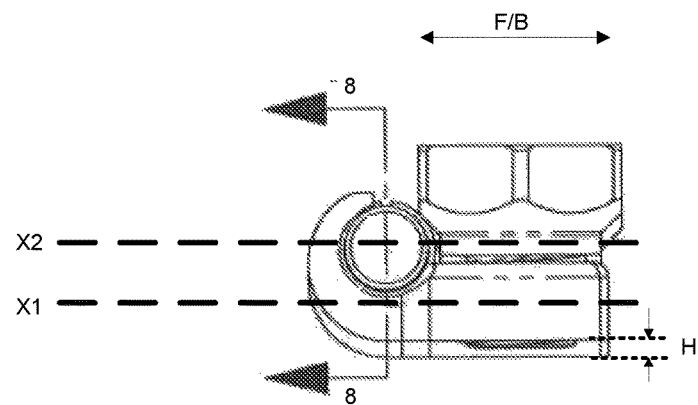
FIG. 7 is a side view of the transverse connector of FIG. 1 as illustrated in FIG. 6.
Figure 8:
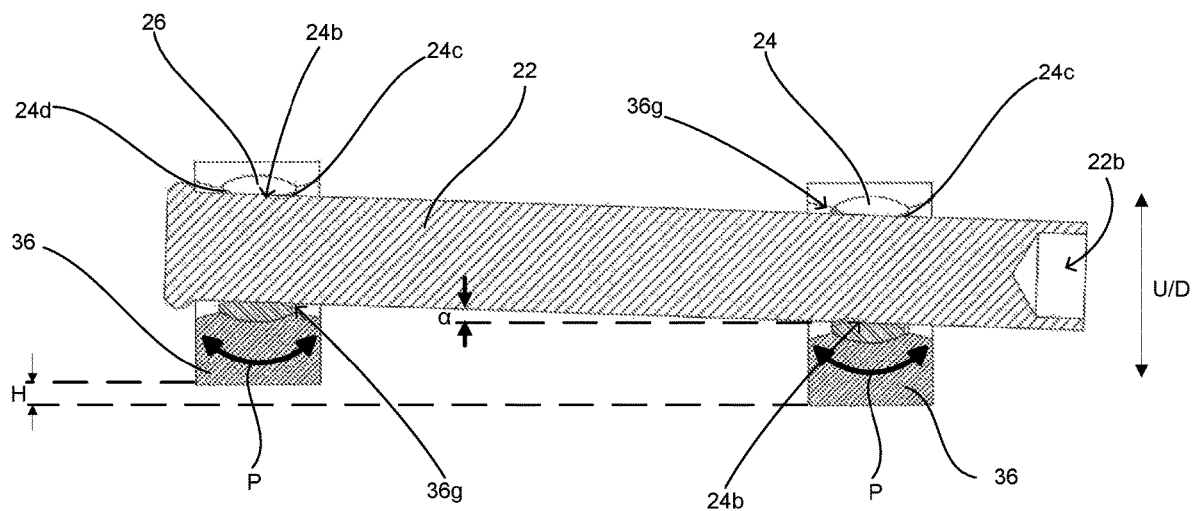
FIG. 8 is an enlarged, cross-sectional view of the transverse connector as illustrated in FIG. 6 and taken along section line 8-8 shown in FIG. 7.

As seen in FIGS. 6-8, second connector assembly 40 can be moved, for example, relative to first connector assembly 30 (e.g., a height "H"), or vice versa, so that cross member 22 is at an angle "α" and first and second connector assemblies 30, 40 are vertically offset from one another. Angle "α" can be any suitable angle and may range between about 0 and 15 degrees of polyaxial motion, which may be positive or negative depending on respective positions of connector assemblies 30, 40. In particular, each of rings 24, 26 is polyaxially supported in one of the ring grooves 36g of respective first and second connector assemblies 30, 40, as indicated by arrows "P," for example, so that rings 24, 26 pivot about respective axes "X1" and "X2" as one or both of first and second connector assemblies 30, 40 are displaced relative to one another (e.g., vertically, horizontally, or both).

With reference to FIGS. 4-9, a spinal system 100 may include a transverse connector 10 coupled to bone anchors 50, 60 that support spinal rods "R1" and "R2" therein, respectively. Spinal rods "R1" and "R2" can also be coupled to one or more additional bone anchors 50a, 50b, 60a, 60b, etc. via set screws "SS."

In operation, distal portions of screws 34 of first and second connector assemblies 30, 40 can be threadably coupled to threaded inner surfaces 52a of heads 52 of bone anchors 50, 60, respectively secured to one or more vertebral bodies "V" of a spine "S." And, with cross member assembly 20 coupled to mounts 36 of first and second connector assemblies 30, 40, such that cross member 22 is axially movable relative to first and second connector assemblies 30, 40 and first and second rings 24, 26 for selectively adjusting a distance between first and second connector assemblies 30, 40, screws 34 of first and second connector assemblies 30, 40 can be received in mounts 36 of first and second connector assemblies 30, 40. Once mounts 36 are positioned on a proximal end portion of screws 34, nuts 32 of first and second connector assemblies 30, 40 can be threaded onto proximal portions of screws 34 to secure transverse connector 10 to bone anchors 50, 60. As nuts 32 tighten down on screws 34, distal taper portions 32x of nuts 32 (see FIG. 3) engage respective first and second rings 24, 26. Further tightening of nuts 32 causes first and second rings 24, 26 to compress around cross member 22 to frictionally lock cross member 22 (as well as first and second connector assemblies 30, 40) in position (e.g., axially fixed). In particular, diameters of first and second rings 24, 26 shrink when slots 24a (FIG. 2) of first and second rings 24, 26 close, as indicated by arrows "C" (FIG. 3), in response to radial compression imparted thereto from axial translation of nuts 32 along screws 34, as indicated by arrows "T" (FIG. 1), when nuts 32 are rotated in a tightening direction about screws 34, as indicated by arrows "R" (FIG. 1).

Adjustment of spinal rods "R1" and/or "R2" can be effectuated upon selective untightening and/or retightening of nuts 32 of transverse connector 10 and/or of set screws "SS" of bone anchors 50a, 50b, 60a, 60b, etc. as desired. In particular, when nuts 32 are loosened, spinal rods "R1" and/or "R2" can be manipulated as necessary. Once spinal rods "R1" and/or "R2" positioned as desired, nuts 32 of transverse connector 10 and/or of set screws "SS" of bone anchors 50a, 50b, 60a, 60b, etc. can be retightened to fix spinal rods "R1" and/or "R2" in position.

Any of the presently disclosed devices can also be provided as a kit, which includes at least one of the transverse connectors. The kit can also include additional orthopedic devices and instruments; such as for example, instruments for tightening or loosening the locking screws, spinal rods, hooks or links and any additional instruments or tools associated therewith. Such a kit can be provided with sterile packaging to facilitate opening and immediate use in an operating room.

Any of the presently disclosed devices, or components thereof, can be formed of any suitable biocompatible material or combinations of materials for use in surgical procedures such as mixed metallic materials like titanium, titanium alloy (e.g., Ti-6Al-4V), stainless steel, and cobalt chrome alloy.

Any of the presently disclosed embodiments, or components thereof, can be formed or secured together using any suitable technique such as welding, fastening, machining, molding, press-fit, etc., or combinations thereof.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A transverse connector comprising:
    a cross member assembly including a cross member, a first ring, and a second ring, the cross member having a first end portion and a second end portion, the first ring receivable on the first end portion of the cross member and the second ring receivable on the second end portion of the cross member; and first and second connector assemblies coupled to the first and second rings of the cross member assembly, respectively, to support the cross member between the first and second connector assemblies;
wherein the first connector assembly includes a mount, a screw detachably coupleable with the mount, and a nut that threadably engages the screw,
wherein the screw is configured to threadably secure the first connector assembly to a first bone anchor,
wherein the nut includes a drive portion and a skirt that extends distally from the drive portion, and
wherein the drive portion includes a distal taper portion that is selectively engagable with the first ring as the nut rotates about the screw.

2. The transverse connector of claim 1, wherein the mount is configured to seat the first connector assembly on the first bone anchor.

3. The transverse connector of claim 2,
wherein the screw is coupleable with the mount by receiving the screw through the mount, and
wherein the screw is engagable with the first bone anchor.

4. The transverse connector of claim 1, wherein the nut threadably engages the screw to selectively secure the first connector assembly to the first bone anchor.

5. The transverse connector of claim 4, wherein the nut is configured to tighten against the first ring to tighten the first ring around the cross member and fictionally lock the cross member in position relative to the first connector assembly.

6. The transverse connector of claim 2, wherein the mount includes a head mount portion and a rod mount portion that extends from the head mount portion, the rod mount portion configured to receive the cross member.

7. The transverse connector of claim 6, wherein the rod mount portion includes a hooked arm that curves upward and inward toward the head mount portion.

8. The transverse connector of claim 7, wherein the hooked arm defines a ring groove that is configured to receive the first ring therein.

9. The transverse connector of claim 8, wherein the first ring is an open ended ring positioned to move between a first position and second position, the first ring having a first diameter in the first position and a second diameter in the second position, the second diameter being less than the first diameter.

10. The transverse connector of claim 9, wherein the first ring is configured to axially lock the cross member to the rod mount portion of the mount when the first ring is in the second position.

11. The transverse connector of claim 10, wherein the cross member is axially movable relative to the first ring when the first ring is in the first position.

12. The transverse connector of claim 1, wherein the cross member includes an annular flange supported on one of the first and second end portions of the cross member, the annular flange configured to limit axial movement of the cross member relative to the first and second connector assemblies.

13. A transverse connector comprising:
a cross member including a first end portion and a second end portion;
a ring supported on the first end portion of the cross member;
a first connector assembly coupled to the ring to secure the cross member to the connector assembly; and
a second connector assembly coupled to the second end portion of the cross member,
wherein the first connector assembly includes a mount, a screw detachably coupleable with the mount, and a nut that engages the screw,
wherein the screw is configured to threadably secure the first connector assembly to a first bone anchor,
wherein the nut includes a drive portion and a skirt that extends distally from the drive portion, and
wherein the drive portion includes a distal taper portion that is selectively engagable with the ring as the nut rotates about the screw.

14. The transverse connector of claim 13,
wherein the screw is coupleable with the mount by receiving the screw through the mount, and
wherein the nut couples to the screw to secure the cross member to the mount.

15. The transverse connector of claim 13, wherein the nut and the screw are threadably coupled together.

16. The transverse connector of claim 1, wherein the ring is configured to compress against the cross member as the nut tightens against the ring.

17. The transverse connector of claim 13, wherein the mount includes a hooked arm that supports the ring and the cross member therein.

18. A spinal system, comprising:
a first bone anchor configured to support a first spinal rod;
a second bone anchor configured to support a second spinal rod; and
a transverse connector that couples the first and second bone anchors together, the transverse connector including:
a first connector assembly including a first mount coupled to the first bone anchor and supporting a first ring, a screw detachably coupleable with the first mount, and a nut that threadably engages the screw, wherein the screw is configured to threadably secure the first connector assembly to the first bone anchor,
wherein the nut includes a drive portion and a skirt that extends distally from the drive portion, and
wherein the drive portion includes a distal taper portion that is selectively engagable with the first ring as the nut rotates about the screw;
a second connector assembly including a second mount coupled to the second bone anchor and supporting a second ring; and
a cross member coupled to the first and second rings and extending between the first and second connector assemblies.

* * * * *